United States Patent
Hou et al.

(10) Patent No.: US 12,392,853 B2
(45) Date of Patent: Aug. 19, 2025

(54) SYSTEM AND METHOD FOR TISSUE CHARACTERIZATION USING FAST QUANTITATIVE SPIN-LOCK MAGNETIZATION TRANSFER IMAGING

(71) Applicant: The Chinese University of Hong Kong, Shatin (CN)

(72) Inventors: Jian Hou, Xincheng Town (CN); Weitian Chen, Ma An Shan (CN)

(73) Assignee: The Chinese University of Hong Kong, N.T. (CN)

( * ) Notice: Subject to any disclaimer, the term of this patent is extended or adjusted under 35 U.S.C. 154(b) by 0 days.

(21) Appl. No.: 18/101,088

(22) Filed: Jan. 24, 2023

(65) Prior Publication Data
US 2023/0236273 A1 Jul. 27, 2023

Related U.S. Application Data

(60) Provisional application No. 63/302,904, filed on Jan. 25, 2022.

(51) Int. Cl.
*G01R 33/56* (2006.01)
*A61B 5/055* (2006.01)
*G01R 33/44* (2006.01)

(52) U.S. Cl.
CPC .......... *G01R 33/5605* (2013.01); *A61B 5/055* (2013.01); *G01R 33/446* (2013.01); *G01R 33/5608* (2013.01)

(58) Field of Classification Search
CPC .. A61B 5/055; G01R 33/446; G01R 33/5605; G01R 33/5608
See application file for complete search history.

(56) References Cited

U.S. PATENT DOCUMENTS

| | | | |
|---|---|---|---|
| 5,050,609 A | 9/1991 | Balaban et al. | |
| 5,281,917 A | 1/1994 | Santyr | |
| 5,317,264 A | 5/1994 | Rommel et al. | |
| 9,341,692 B2 | 5/2016 | Mangia et al. | |
| 9,709,511 B2 | 7/2017 | Lee et al. | |
| 10,101,423 B2* | 10/2018 | Devience | G01R 33/4608 |

(Continued)

FOREIGN PATENT DOCUMENTS

| | | |
|---|---|---|
| CN | 1458536 A | 11/2003 |
| CN | 102652672 A | 9/2012 |

(Continued)

OTHER PUBLICATIONS

Jin, et al. "Quantitative Chemical Exchange Sensitive MRI Using Irradiation with Toggling Inversion Preparation," Magnetic resonance in medicine, vol. 68, No. 4, pp. 1056-1064 (2012).

(Continued)

*Primary Examiner* — Gregory H Curran
(74) *Attorney, Agent, or Firm* — Kilpatrick Townsend & Stockton LLP

(57) ABSTRACT

Systems and methods for fast and robust quantification of magnetization transfer (MT) use off-resonance spin-lock MRI with as few as two or three image acquisitions. Each image acquisition can be performed using an off-resonance spin-lock pulse having a different RF amplitude and frequency offset. A parameter representing the difference of the relaxation rate in the rotating frame between the acquisitions can be computed. This parameter can be used to compute other parameters of magnetization transfer.

20 Claims, 6 Drawing Sheets

(56) References Cited

U.S. PATENT DOCUMENTS

| | | | |
|---|---|---|---|
| 10,551,455 B2* | 2/2020 | Wendell | G01R 33/4838 |
| 2009/0009168 A1 | 1/2009 | Witschey et al. | |
| 2010/0026297 A1 | 2/2010 | Sun et al. | |
| 2010/0166284 A1 | 7/2010 | Smith et al. | |
| 2010/0264920 A1 | 10/2010 | Witschey et al. | |
| 2012/0019244 A1 | 1/2012 | Chen et al. | |
| 2013/0178734 A1 | 7/2013 | Wald et al. | |
| 2017/0315198 A1 | 11/2017 | Chen et al. | |
| 2018/0031661 A1* | 2/2018 | Chen | G01R 33/56563 |
| 2018/0038928 A1 | 2/2018 | Wiesinger et al. | |
| 2019/0033412 A1 | 1/2019 | Alsop et al. | |

FOREIGN PATENT DOCUMENTS

| | | | |
|---|---|---|---|
| CN | 102859386 A | 1/2013 | |
| CN | 103328999 A | 9/2013 | |
| CN | 103477239 A | 12/2013 | |
| CN | 104914389 A | 9/2015 | |
| CN | 105358998 A | 2/2016 | |
| CN | 107669272 A | 2/2018 | |
| CN | 108139454 A | 6/2018 | |
| CN | 108175409 A | 6/2018 | |
| CN | 110140042 A | 8/2019 | |
| KR | 20120017275 A | 2/2012 | |
| WO | 90/10878 A1 | 9/1990 | |
| WO | 2017196878 A1 | 11/2017 | |
| WO | 2018185496 A2 | 10/2018 | |

OTHER PUBLICATIONS

Smith, et al. "Rapid, high-resolution quantitative magnetization transfer MRI of the human spinal cord," NeuroImage, vol. 95, pp. 106-116 (2014).

Zaiss, et al. "A combined analytical solution for chemical exchange saturation transfer and semi-solid magnetization transfer," NMR in biomedicine, vol. 28, No. 2, pp. 217-230 (2015).

Hou, et al., "Macromolecular proton fraction mapping based on spin-lock magnetic resonance imaging," Magnetic Resonance in Medicine, pp. 1-15. (2020).

Jiang, et al., "Probing chemical exchange using quantitative spin-lock R1 p asymmetry imaging with adiabatic RF pulses," Magn Reson Med., vol. 82(5), pp. 1767-1781 (2019).

Jiang, et al., "On-resonance and off-resonance continuous wave constant amplitude spin-lock and T1p quantification in the presence of B1 and B0 inhomogeneities," NMR Biomed, vol. 31(7):e3928., 17 pages (2018).

Chen, et al., "Artifacts correction for T1rho imaging with constant amplitude spin-lock," Journal of Magnetic Resonance, vol. 274, pp. 13-23 (2017).

Chen, et al., "Breath-hold black blood quantitative T1rho imaging of liver using single shot fast spin echo acquisition," Quant Imaging Med Surg., vol. 6(2), pp. 168-177 (2016).

Zaiss, Moritz, etal. A contact analytical solution for chemicals exchange saturation transfer and semi-solid magnetization transfer. Nmr in Biomedicine 28.2(2015):217-230.

Smith AK, Dortch RD, Dethrage LM, Smith SA. Rapid, high-resolution quantitative magnetization transfer MRI of the human spinal cord. Neuroimae. Jul. 15, 2014:106-16. doi: 10.1016/j.neuroimage.2014.03.005. Epub Mar. 13, 2014. PMID: 24632465; PMCID: PMC4052565.

Jin, Kim, and S.-G. Quantitative chemical exchange sensitive MRI using irradiation with toggling inversion preparation. Magnetic resonance in medicine: official journal of the Society of Magnetic Resonance in Medicine (2012).

* cited by examiner

SYSTEM AND METHOD FOR TISSUE CHARACTERIZATION USING FAST QUANTITATIVE SPIN-LOCK MAGNETIZATION TRANSFER IMAGING

CROSS-REFERENCE TO RELATED APPLICATION

This application claims priority to U.S. Provisional Application No. 63/302,904, filed Jan. 25, 2022, the disclosure of which is incorporated herein by reference.

BACKGROUND

This disclosure relates generally to magnetic resonance imaging (MRI) techniques, and in particular to techniques for fast quantitative spin-lock magnetization transfer imaging for tissue characterization.

Magnetic resonance imaging (MRI) is a noninvasive diagnostic technique that can allow assessments of the composition and state of various tissues. In an MRI procedure, a patient is placed in a strong longitudinal magnetic field (B0) that aligns nuclear spins of atoms in the patient's body, producing a net magnetization vector. RF pulses with magnetic field components (B1) transverse to the longitudinal field and frequencies tuned to the Larmor frequency of an isotope of interest (often $_1$H) are applied. These pulses can flip spins into a higher energy state, resulting in a transverse component to the magnetization vector. As these spins return to the ground state, responsive RF pulses from the patient's body can be detected. Based on the response to pulses, characteristics of the magnetization can be measured. Commonly used measurements include the spin-lattice relaxation time (T1), measurement of which is typically based on recovery of the longitudinal component of the magnetization vector, and the spin-spin relaxation time (T2), measurement of which is typically based on decay of the transverse component of the magnetization vector. Since different anatomical structures have different material compositions, quantification of T1 and/or T2 can provide information about the material composition of a structure being imaged, and particular pulse sequences can be optimized to quantify T1 or T2. Spin-lattice relaxation time in the rotating frame, known as $T_{1\rho}$ (or $R_{1\rho}=1/T_{1\rho}$), is a magnetization characteristic that is sensitive to molecular interactions, including dipolar interactions, chemical exchange, and magnetization transfer. $R_{1\rho}$ quantification is typically performed using on-resonance spin-lock MRI. However, $R_{1\rho}$ relaxation also occurs during off-resonance spin-lock.

In addition to providing high-quality anatomical images of tissues, MRI can be used to examine tissue at a molecular level. For instance, it is possible to measure magnetization transfer (MT) effects, in which magnetization is transferred between protons of mobile water (commonly referred to as the "free pool") and protons associated with semi-solid macromolecules such as lipids and other complex molecules (commonly referred to as the "bound pool"). The protons of the bound pool have ultrashort T2 relaxation and therefore a significantly broader absorption lineshape compared to the mobile protons. Applying off-resonance saturation RF pulses during an MRI procedure allows protons of the bound pool to be selectively saturated while keeping the mobile protons unaffected. The saturation is transferred to the free-water pool due to dipolar interactions and chemical exchange, resulting in MT contrast.

MT ratio (MTR) is commonly used to characterize magnetization transfer. However, MTR is not an intrinsic tissue property because it is influenced by the pulse sequence parameters. Quantitative MT approaches have been developed to measure tissue-specific MT parameters based on a two-pool model having a free-water pool and a bound pool as described above. The model specifies parameters including T1 and T2 for each pool, magnetization exchange rates between the two pools, and the molar fraction of protons that are bound to macromolecules, also known as bound pool fraction (BPF) or macromolecular proton fraction (MPF). MPF is a tissue-specific parameter that is directly linked to the macromolecular density and composition and is independent of acquisition parameters.

In clinical applications, however, extracting MPF from MRI data is challenging, in part because of the need to quantify multiple MT parameters, which requires multiple MRI scans using different acquisition parameters and complicated post-processing. Acquisition time can be reduced by estimating only the most clinically relevant parameters, including MPF. Various techniques have been proposed. Some of these techniques use a single off-resonance RF saturation measurement, combined with assumptions that cross-relaxation is sufficiently fast and that a T1 map has already been acquired (e.g., using additional MRI scans). Another approach involves labeling the spins of the mobile protons rather than saturating off-resonance spins associated with the bound pool, using techniques such as stimulated echo amplitude modulation (STEAM) and fitting to a monoexponential longitudinal relaxation model at steady state. This avoids the need to acquire a T1 map; however, stimulated echo techniques have intrinsically low signal-to-noise. Accordingly, faster and more accurate techniques for MPF quantification would be desirable.

SUMMARY

Certain embodiments of the present invention relate to systems and methods for tissue characterization using fast quantitative spin-lock magnetic transfer imaging. The techniques can be insensitive to variations of the inherent relaxation rates R1 (1/T1) and R2 (1/T2) of the free-water pool and to variations of the chemical exchange pool. The techniques can also be robust in the presence of inhomogeneity in the B1 RF and/or B0 magnetic fields.

Some embodiments relate to methods for quantifying parameters of magnetization transfer using an MRI apparatus. Such methods can include: performing a first image acquisition process to produce a first MRI image, wherein the first image acquisition process includes applying an off-resonance spin-lock pulse having a first RF amplitude ($\omega_1^{(1)}$), a first frequency offset ($\Delta\omega^{(1)}$), and a time of spin-lock (TSL); performing a second image acquisition process to produce a second MRI image, wherein the second image acquisition process includes applying an off-resonance spin-lock pulse having an RF amplitude ($\omega_1^{(2)}$) and a frequency offset ($\Delta\omega^{(2)}$); and computing, based on the first and second MRI images, one or more parameters of magnetization transfer, wherein the one or more parameters of magnetization transfer include a parameter $R_{mts1}$ defined as $R_{mts1}=R_{1\rho}^{(2)}-R_{1\rho}^{(1)}$, where $R_{1\rho}^{(1)}$ is a first relaxation rate in the rotating frame responsive to a spin-lock pulse having the first RF amplitude $\omega_1^{(1)}$ and the first frequency offset $\Delta\omega^{(1)}$ and $R_{1\rho}^{(2)}$ is a second relaxation rate in the rotating frame responsive to a spin-lock pulse having the second RF amplitude $\omega_1^{(2)}$ and the second frequency offset $\Delta\omega^{(2)}$.

DETAILED DESCRIPTION

Examples (also referred to as "embodiments") of systems and methods that provide quantification of parameters of magnetization transfers are described in this section. According to these and other embodiments, parameters of magnetization transfer can be quantified using spin-lock magnetic resonance imaging (MRI) techniques. It is noted that spin-lock also occurs during saturation RF pulses; accordingly, in embodiments described herein, off-resonance spin-lock RF pulse clusters or saturation RF pulses can be applied, and the term "spin-lock pulse" is used to refer to both spin-lock pulse clusters and saturation RF pulses. A series of acquisitions can be performed to provide a final measurement that is specific to the MT pool and independent of the free-water pool and the chemical exchange pool. As will become apparent, embodiments described herein allow quantification of magnetization transfer without acquisition of a T1 map or any assumption about the relaxation properties of the free-water pool.

MRI Systems

Figure 1:
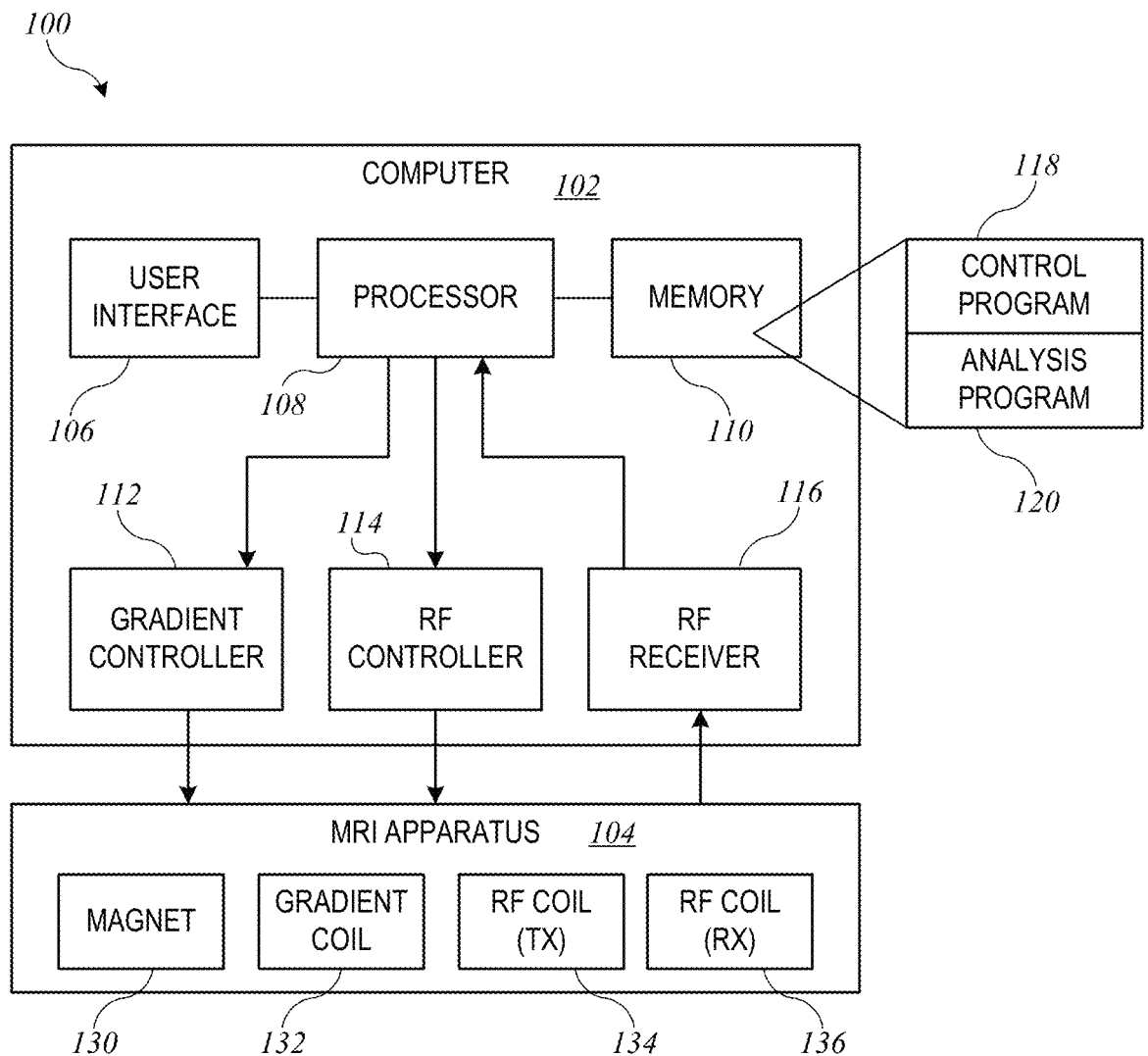
FIG. 1 shows an MRI system that can be used in connection with practicing some embodiments of the present invention.

FIG. 1 shows an MRI system that can be used in connection with practicing some embodiments of the present invention. MRI system 100 includes a computer 102 communicably coupled to an MRI apparatus 104.

Computer 102 can be of generally conventional design and can include a user interface 106, a processor 108, a memory 110, a gradient controller 112, an RF controller 114, and an RF receiver 116. User interface 106 can include components that allow a user (e.g., an operator of MRI system 100) to input instructions or data and to view information. For example, user interface 106 can include a keyboard, mouse, joystick, display screen, touch-sensitive display screen, and so on. Processor 108 can include a general purpose programmable processor (or any other processor or set of processors) capable of executing program code instructions to perform various operations. Memory 110 can include a combination of volatile and nonvolatile storage elements (e.g., DRAM, SRAM, flash memory, magnetic disk, optical disk, etc.). Portions of memory 110 can store program code to be executed by processor 108. Examples of the program code can include a control program 118, which can coordinate operations of MRI apparatus 104 as described below in order to acquire data, and an analysis program 120, which can perform analysis algorithms on data acquired from MRI apparatus 104 (e.g., as described below). Gradient controller 112, RF controller 114, and RF receiver 116 can incorporate standard communication interfaces and protocols to communicate with components of MRI apparatus 104 as described below.

MRI apparatus 104 can be of generally conventional design and can incorporate a magnet 130, a gradient coil 132, and RF coils 134, 136. Magnet 130 can be a magnet capable of generating a large constant magnetic field B0 (e.g., 1.5 T, 3.0 T, or the like) in a longitudinal direction, in a region where a patient (or other subject to be imaged) can be placed. Gradient coil 132 can be capable of generating gradients in the constant magnetic field B0; operation of gradient coil 132 can be controlled by computer 102 via gradient controller 112. RF coils 134, 136 can include a transmitter (TX) coil 134 and a receiver (RX) coil 136. In some embodiments, a single coil can serve as both transmitter and receiver. In some embodiments, RF transmitter coil 134 can be placed around the portion of the subject's body that is to be imaged while RF receiver coil 136 is placed elsewhere within MRI apparatus 104. The preferred placement of RF coils 134, 136 may depend on the specific portion of the body that is to be imaged; those skilled in the art with access to the present disclosure will be able to make appropriate selections.

In operation, computer 100 can drive gradient coil 132 using gradient controller 112 to shape the magnetic field around the region being imaged. Computer 100 can drive RF transmitter coil 134 using RF controller 114 to generate RF pulses at a desired frequency (e.g., a resonant frequency for an isotope of interest), driving nuclear spins into an excited state. RF receiver coil 136 can detect RF waves generated by the spins relaxing from the excited state when RF pulses are not being generated. RF receiver 116 can include amplifiers, digital-to-analog converters, and other circuitry to generate digital data from the RF waves detected by RF receiver coil 136. RF receiver 116 can provide this data to processor 108 for analysis.

MRI system 100 is illustrative, and many variations and modifications are possible. Those skilled in the art will be familiar with a variety of MRI apparatus and control systems and with basic principles of MRI data acquisition, including the use of gradient fields and RF pulses, as well as techniques for detecting signals responsive to RF pulses and processing those signals to generate images.

In some embodiments, MRI system 100 or other MRI apparatus can be used to generate pulse sequences suitable for MT imaging of a subject, such as a specific organ or tissue within a patient. Examples of pulse sequences and imaging operations are described below.

Typical MRI imaging processes include a "preparation" phase and an "acquisition" phase. During the preparation phase, various pulse sequences can be generated in RF transmitter coil 136 to create a desired state of the magnetization vectors of nuclei of interest. For instance, a "reset" sequence may be used to reset net magnetization such that net magnetization becomes zero. Other types of preparation can include pulse sequences designed to suppress signals from specific types of tissue not of interest (e.g., blood, fat). In embodiments described herein, the magnetization preparation sequence can include a spin-lock RF pulse cluster or a saturation RF pulse. A spin-lock RF pulse cluster consists of a tip-down RF pulse, a spin-lock RF pulse, and a tip-up RF pulse. A saturation RF pulse includes a spin-lock RF pulse without a tip-down RF pulse or tip-up RF pulse. Spin-lock can also occur during a saturation RF pulse, and the term "spin-lock pulse" is used herein to encompass a spin-lock RF pulse cluster or a saturation RF pulse (or other pulses or pulse clusters during which spin-lock occurs). The spin-lock RF pulse or saturation RF pulse is applied for a specified time duration (referred to as the time of spin-lock, or TSL). Some magnetization preparation sequences can also include a toggling RF pulse. After the preparation phase, acquisition can be performed using various sequences such as fast spin echo sequences or other sequences as desired.

MPF Quantification Process

Certain embodiments described herein provide quantification of parameters of magnetization transfer (MT), such as macromolecular proton fraction (MPF). In some embodiments, a two-pool model is used, in which the measured relaxation rate is based on contributions from two different magnetization pools: a free-water pool (also referred to as "pool a") and a pool of protons bound to macromolecules (also referred to as a "bound pool" or "pool b"). The model assumes that magnetization exchanges can occur between the free-water and bound pools at some rate. The fractional sizes of the two pools are initially unknown. The notation shown in Table 1 is used to denote various parameters of the two pools.

TABLE 1

| | |
|---|---|
| $R_{1a} = 1/T_{1a}$ | Longitudinal relaxation rate of pool a (free-water pool) |
| $R_{1b} = 1/T_{1b}$ | Longitudinal relaxation rate of pool b (bound pool) |
| $R_{2a} = 1/T_{2a}$ | Transverse relaxation rate of pool a |
| $R_{2b} = 1/T_{2b}$ | Transverse relaxation rate of pool b |
| $f_a, f_b$ | Pool size ratios of pools a and b ($f_a = 1$) |
| $k_{ba}, k_{ab}$ | Exchange rates between pool b and pool a |

According to the two-pool model, for a spin-lock pulse having an RF amplitude $\omega_1$ and resonance frequency offset $\Delta\omega$, the relaxation rate during spin-lock ($R_{1\rho}$) can be derived by solving the Bloch-McConnell equation:

$$R_{1\rho}(\Delta\omega,\omega_1) = R_{water}(\Delta\omega,\omega_1) + R_{mt}(\Delta\omega,\omega_1), \quad (1)$$

where $R_{water}$ is the effective relaxation rate of the water in the rotating frame and $R_{mt}$ is the MT-dependent relaxation rate. The effective relaxation rate $R_{water}$ can be expressed as:

$$R_{water} = R_{1a}\cos^2\theta + R_{2a}\sin^2\theta, \quad (2)$$

where $$\sin^2\theta = \frac{\omega_1^2}{\omega_1^2 + \Delta\omega^2}, \quad \cos^2\theta = \frac{\Delta\omega^2}{\omega_1^2 + \Delta\omega^2}. \quad (3)$$

The MT-dependent relaxation rate $R_{mt}$ can be expressed as:

$$R_{mt} = \frac{(\Delta\omega^2 + r_{2a}^2)(k_{ba}r_{1a} + r_{1b}(k_{ab} + r_{1a})) + \omega_1^2 r_{2a}(k_{ba} + r_{1b})}{(\Delta\omega^2 + r_{2a}^2)(k_{ab} + k_{ba} + r_{1a} + r_{1b}) + 2r_{2a}(k_{ba}r_{1a} + r_{1b}(k_{ab} + r_{1a})) + \omega_1^2(r_{2a} + k_{ba} + r_{1b})}, \quad (4)$$

where $r_{1a} = R_{1a} - R_{water}$; $r_{2a} = R_{2a} - R_{water}$; and $r_{1b} = R_{1b} + R_{rfc} - R_{water}$, where $R_{rfc}$ represents the saturation rate of the bound pool. The saturation rate of the bound pool $R_{rfc}$ is a function of the RF amplitude ($\omega_1$), off-resonance frequency ($\Delta\omega$), and $T_{2b}$. In some embodiments, $R_{rfc}(\Delta\omega) = \omega_1^2 \pi g_b(\Delta_{co})$, where $$g_b(\Delta\omega) = T_{2b}\int_0^1 \frac{1}{|3u^2 - 1|}\sqrt{\frac{2}{\pi}}\exp\left(-2\left(\frac{\Delta\omega \cdot T_{2b}}{3u^2 - 1}\right)^2\right)du \quad (5)$$

is the super-Lorentzian lineshape for the bound pool. Other lineshapes, such as Gaussian lineshape, can also be used in some embodiments. A derivation of Eq. (4) as an analytical expression of MT-dependent relaxation based on the eigenspace solution of the Bloch-McConnell equation has been shown in Zaiss et al., "A combined analytical solution for chemical exchange saturation transfer and semi-solid magnetization transfer," NMR in *Biomedicine* 28(2):217-30 (2015).

Macromolecular proton fraction (MPF) can be defined as $$MPF = \frac{f_b}{1 + f_b}. \quad (6)$$

According to some embodiments, MPF can be quantified by measuring the difference of $R_{1\rho}$ from two determinations at two different combinations of off-resonance frequency and RF amplitude of the spin-lock pulse. (It should be understood that for off-resonance spin-lock, $\Delta\omega \neq 0$; for on-resonance spin-lock, $\Delta\omega = 0$.) This parameter is defined as $R_{mts1}$. Specifically:

$$R_{mts1} = R_{1\rho}{}^{(2)} - R_{1\rho}{}^{(1)} = R_{1\rho}(\Delta\omega^{(2)}, \Delta\omega^{(1)}) - \Delta R_{1\rho}(\Delta\omega^{(1)}, \omega_1{}^{(1)}) = \Delta R_{water} + \Delta R_{mt}, \quad (7)$$

where superscripts $^{(1)}$ and $^{(2)}$ denote the different acquisitions. A derivation of $R_{mts1}$ and the quantitative relationship between $R_{mts1}$ (also referred to as $R_{mpfs1}$) and MPF have been previously published in U.S. Patent Application Pub. No. 2021/0141041 A1.

If the off-resonance frequencies and RF amplitudes for the two acquisitions satisfy the following condition:

$$\Delta\omega^{(1)}/\omega_1{}^{(1)} = \Delta\omega^{(2)}/\omega_1{}^{(2)}, \quad (8)$$

then Eq. (3) gives $\theta^{(1)} = \theta^{(2)}$, and Eq. (2) yields $\Delta R_{water} = 0$.

The magnetization model of each acquisition can be expressed as:

$$M = M_{ini}e^{-R_{1\rho}(\omega_1,\Delta\omega)TSL} + M_{ss}(1 - e^{-R_{1\rho}(\omega_1,\Delta\omega)TSL}), \quad (9)$$

where $M_{ini}$ is the initial magnetization just before spin-lock, $\omega_1$ is the, RF amplitude TSL is the time of spin-lock, $M_{ss} = M_0 R_1 \cos\theta/R_{1\rho}$ is the steady-state magnetization, $M_0$ is the equilibrium magnetization, $R_1$ is the longitudinal relaxation rate of water protons, and $\theta$ is given by $\theta = \arctan(\omega_1/\Delta\omega)$. Note that $M_{ini}{}^{(1)} = M_{ini}{}^{(2)}$ and $\theta^{(1)} = \theta^{(2)}$ when Eq. (8) is satisfied.

If $R_{1\rho}(\omega_1, \Delta\omega)TSL \ll 1$ for each spin-lock pulse, Eq. (9) can be greatly simplified by applying the first-order approximation of the Maclaurin series expansion $e^{-R_{1\rho}(\omega_1,\Delta w)TSL} \approx 1 - R_{1\rho}(\omega_1, \Delta\omega)TSL$, which yields:

$$M = M_{ini}(1 - R_{1\rho}(\omega_1,\Delta\omega)TSL) + M_0 R_1 TSL \cos\theta \quad (10)$$

or $$M = M_{ini}e^{-R_{1\rho}(\omega_1,\Delta\omega)TSL} + M_0 R_1 TSL \cos\theta. \quad (11)$$

$R_{mts1}$ can be obtained from Eq. (7) as:

$$R_{mts1} = \frac{1}{TSL^{(2)}} - \frac{1}{TSL^{(1)}} + \frac{M^{(1)}TSL^{(2)} - M^{(2)}TSL^{(1)}}{M_{ini}TSL^{(1)}TSL^{(2)}}. \quad (12)$$

Based on Eq. (12), $R_{mts1}$ can be calculated from $M^{(1)}$, $M^{(2)}$, and $M_{ini}$. $M^{(1)}$ and $M^{(2)}$ can be determined by measuring $R_{1\rho}$ under different conditions of spin-lock, e.g., two different combinations of RF amplitude $\omega_1$ and off-resonance frequency $\Delta_{co}$ that satisfy Eq. (8).

When TSL is same for each acquisition (i.e., $TSL^{(1)} = TSL^{(2)} = TSL$, Eq. (12) can be reduced to:

$$R_{mtsl} = \frac{M^{(1)} - M^{(2)}}{M_{ini} TSL}. \quad (13)$$

If a magnetization reset RF pulse is applied to set magnetization to zero at the start of a spin-lock pulse sequence, $M_{ini}$ can be expressed as $$M_{ini} = M_0(1 - e^{-R_1 T_{rec}}), \quad (14)$$

where $T_{rec}$ is the recovery time after the magnetization reset RF pulse. When $T_{rec} > T_1$ (where $T_1 = 1/R_1$ is the longitudinal relaxation time of water protons), we have $M_{ini} e^{-R_{1\rho}(\omega_1, \Delta\omega) TSL} >> M_0 R_1 TSL \cos\theta$. Eq. (11) can thus be reduced to $$M = M_{ini} e^{-R_{1\rho}(\omega_1, \Delta\omega) TSL}. \quad (15)$$

Given the same TSL for each spin-lock pulse, $R_{mtsl}$ can be calculated by:

$$R_{mtsl} = -\log\frac{M^{(2)}}{M^{(1)}}/TSL. \quad (16)$$

It should be noted that if the condition that $R_{1\rho}(\omega_1, \Delta\omega)TSL << 1$ is violated, Eq. (13) is still valid under the condition $T_{rec} > T_1$.

In some embodiments, $R_{mtsl}$ can also be obtained using machine learning methods based on the aforementioned theories and equations, which can allow more flexibility in selecting acquisition parameters, including TSL.

According to various embodiments, Eq. (16) forms the basis of an approach to MT quantification. From Eq. (16), it follows that MT can be computed by performing two acquisitions subject to the following conditions: (1) the spin-lock pulses for the two acquisitions satisfy Eq. (8); and (2) $R_{1\rho}(\omega_1, \Delta\omega)TSL << 1$ for each group of spin-lock.

Acquisition Processes for $R_{mtsl}$

As described above, MPF and other magnetization transfer parameters can be determined from one or more measurements of $R_{mtsl}$, which is defined as the difference of $R_{1\rho}$ from two data acquisitions at two different combinations of off-resonance frequency and RF amplitude of the spin-lock pulse. In some embodiments, $R_{1\rho}$ can be measured using off-resonance spin-lock techniques in which a spin-lock RF pulse cluster is applied, followed by imaging data acquisition. A spin-lock RF pulse cluster can include a tip-down RF pulse, a spin-lock RF pulse, and a tip-up RF pulse. The tip-down RF pulse flips the longitudinal magnetization at a specific flip angle determined by the selected spin-lock frequency $\omega_1$ and frequency offset $\Delta\omega$. After the tip-down pulse, the spin-lock RF pulse is applied for a duration in parallel with the magnetization and locks the spin at the specific flip angle. After the spin-lock RF pulse, the tip-up RF pulse flips the spin back to the longitudinal direction. Either hard pulses or adiabatic pulses can be used for the tip-down and tip-up RF pulses. In some embodiments, a saturation RF pulse can be used instead of a spin-lock RF pulse cluster. For saturation RF pulses, there is only a saturation (or spin-lock) RF pulse, with no tip-down or tip-up RF pulse. Where a saturation RF pulse is used, the time duration of the pulse may be much longer than the duration of the spin-lock RF pulse of a spin-lock RF pulse cluster, and the B1 amplitude of the saturation RF pulse may be much smaller than the B1 amplitude of the spin-lock RF pulse of a spin-lock RF pulse cluster. The term "spin-lock pulse" is used herein to encompass a spin-lock RF pulse cluster or a saturation RF pulse (or other pulses or pulse clusters during which spin-lock occurs).

In approaches described herein, $R_{mtsl}$ can be obtained by performing two or three image acquisitions. In a two-acquisition process, under each of two different conditions of spin-lock ($\Delta\omega^{(1)}$, $\omega_1^{(1)}$) and ($\Delta\omega^{(2)}$, $\omega_1^{(2)}$) satisfying Eq. (8) and the constraint that $R_{1\rho}(\omega_1, \Delta\omega)TSL << 1$, an image ($M^{(1)}$ or $M^{(2)}$) is obtained. If the same duration of the spin-lock RF pulse or the saturation RF pulse (TSL) is used for both acquisitions, then $R_{mtsl}$ can be computed according to Eq. (16), Eq. (13), or Eq. (12). If different TSL (denoted as $TSL^{(1)}$ and $TSL^{(2)}$) are used for the two acquisitions, then $R_{mtsl}$ can be computed according to Eq. (12). In a three-acquisition process, the third acquisition can have $TSL^{(3)} = 0$ and can provide an image $M_{ini}$.

Figure 2:
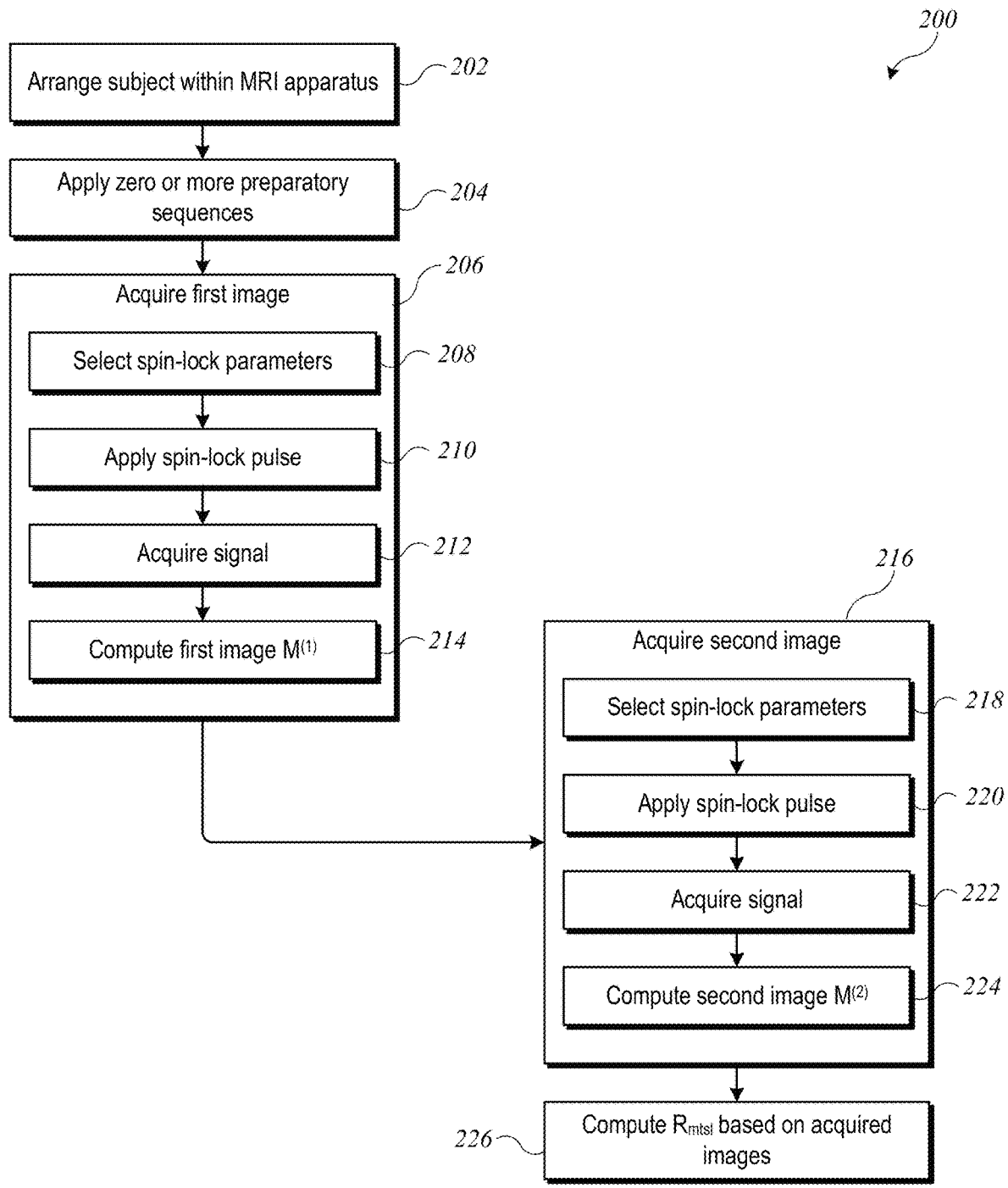
FIG. 2 shows a flow diagram of a process 200 for determining MPF according to some embodiments.

FIG. 2 shows a flow diagram of a two-acquisition process 200 for determining $R_{mtsl}$ according to some embodiments. Process 200 can be performed using an MRI apparatus such as MRI apparatus 100 of FIG. 1. At block 202, a subject (e.g., a patient whose tissue is to be imaged) is arranged within an MRI apparatus. This can include having the patient assume a supine or other desired position and aligning the patient within the MRI apparatus. In some embodiments, this may also include positioning of RF and/or gradient coils; the particular positioning will depend on what is being imaged.

At block 204, various preparatory pulse sequences can be applied. Examples include magnetization reset sequences, sequences to reduce the effect of selected tissue types (e.g., blood, fat, etc.), and the like. Such sequences can be conventional and are optional; a detailed description is omitted as not being critical to understanding the claimed invention.

At block 206, a first image acquisition is performed. In some embodiments, the first image acquisition can include selecting spin-lock parameters ($\Delta\omega^{(1)}$, $\omega_1^{(1)}$, $TSL^{(1)}$) for a first spin-lock pulse (including a spin-lock RF pulse cluster or a saturation RF pulse) at block 208 and applying the spin-lock pulse at block 210, followed by signal acquisition at block 212. Signal acquisition can include generating RF pulses to stimulate a signal from the subject and operating an RF receiver coil to detect the signal. Various acquisition sequences can be performed, including single-shot or multi-shot fast spin echo (FSE) sequences; other acquisition sequences and techniques suitable for quantifying R1ρ can also be used. During the signal acquisition, a first data set can be collected. At block 214, a first image $M^{(1)}$ can be computed based on the first data set. Conventional techniques for generating images from acquired MRI data can be used; examples include Fourier transform of acquired k-space data.

At block 216, a second image acquisition is performed. In some embodiments, the second image acquisition can include selecting spin-lock parameters ($\Delta\omega^{(2)}$, $\omega^{(2)}$, $TSL^{(2)}$) for a second spin-lock pulse (including a spin-lock RF pulse cluster or a saturation RF pulse) at block 218 and applying the spin-lock pulse at block 220, followed by signal acquisition at block 222 to collect a second data set. Signal acquisition operations can be similar or identical to the signal acquisition operations at block 212. At block 224, a second image $M^{(2)}$ can be computed based on the second data set, similarly to computation of the first image at block 214.

At block 226, relaxation parameter $R_{mtsl}$ can be computed from the two images. For instance, if $TSL^{(1)} = TSL^{(2)} = TSL$, then $R_{mtsl}$ can be computed according to Eq. (13) or according to Eq. (16). If $TSL^{(1)}$ and $TSL^{(2)}$ are different, then $R_{mtsl}$ can be computed according to Eq. (12). In some embodiments, machine learning methods can be applied to compute $R_{mts1}$ from the images.

Figure 3:
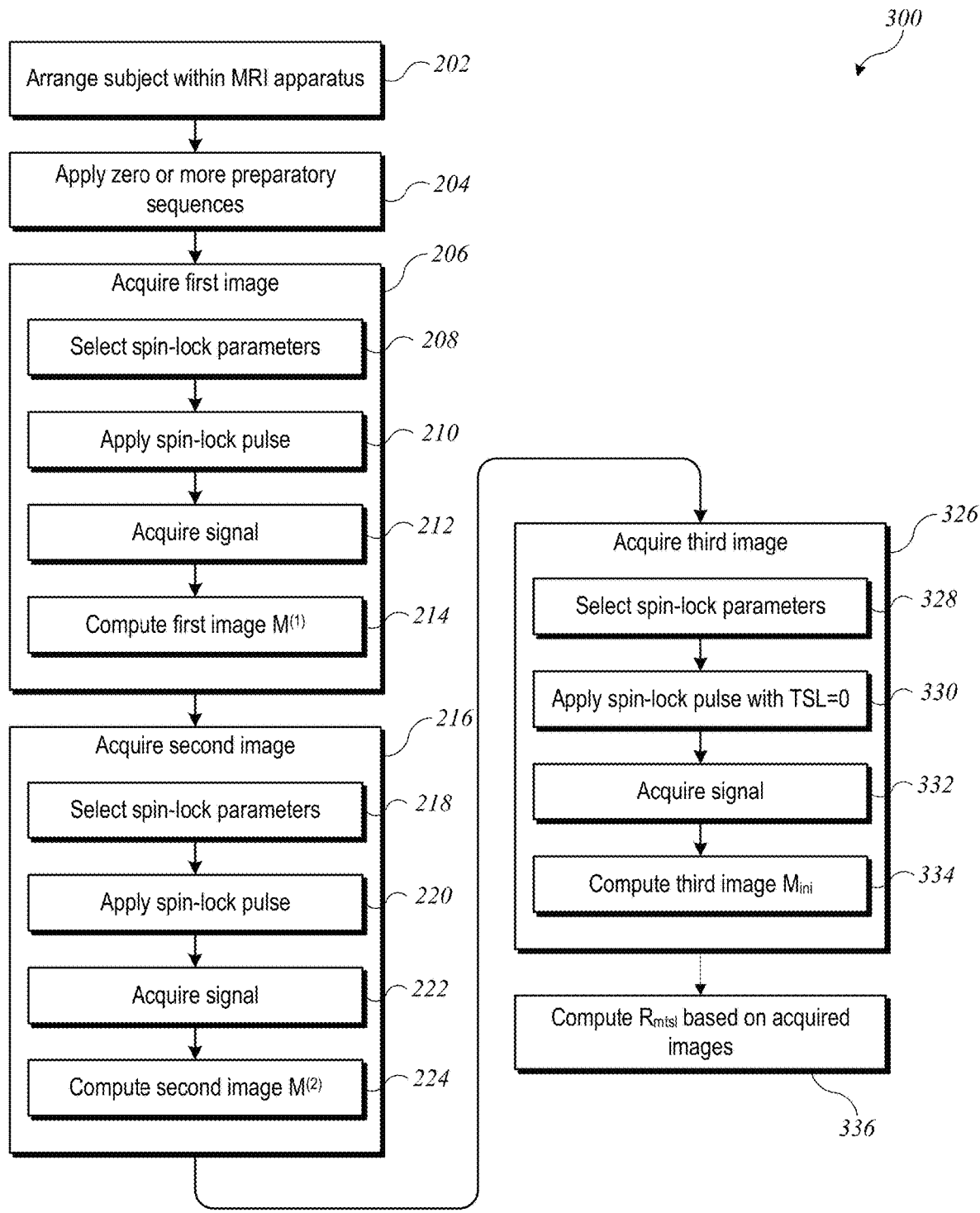
FIG. 3 shows a flow diagram of a process 300 for determining MPF according to some embodiments.

FIG. 3 shows a flow diagram of a three-acquisition process 300 for determining $R_{mts1}$ according to some embodiments. Process 300 can be performed using an MRI apparatus such as MRI apparatus 100 of FIG. 1. Process 300 can include blocks 202-216, which can be similar or identical to the corresponding blocks in process 200 described above, and can also include a third image acquisition at block 326. In some embodiments, the third image acquisition can include selecting spin-lock parameters ($\Delta\omega^{(3)}$, $\omega_1^{(3)}$, $TSL^{(3)}=0$) for a third spin-lock pulse at block 328 and applying the third spin-lock pulse at block 330, followed by signal acquisition at block 332 to collect a third data set. Signal acquisition operations can be similar or identical to the signal acquisition operations at block 212. At block 334, a third image $M_{ini}$ can be computed based on the third data set, similarly to computation of the first image at block 214. At block 336, relaxation parameter $R_{mts1}$ can be computed from the three images. For instance, if $TSL^{(1)}=TSL^{(2)}=TSL$, then $R_{mts1}$ can be computed according to Eq. (13) or according to Eq. (16). If $TSL^{(1)}$ and $TSL^{(2)}$ are different, then $R_{mts1}$ can be computed according to Eq. (12). In some embodiments, machine learning methods can be applied to compute $R_{mts1}$ from the images.

Processes 200 and 300 are illustrative, and variations or modifications are possible. TSL can be chosen as desired, subject to the constraint that the approximations used in deriving Eq. (14) are reliable. For instance, TSL for the first and second image acquisitions can be chosen to be less than 50 ms, and the same TSL can be used for both the first and second image acquisitions. Different acquisitions can be performed in any order; for instance, in a three-acquisition process, an acquisition with TSL=0 can be performed before one or both of the acquisitions with non-zero TSL. Off-resonance frequencies and RF amplitudes for the spin-lock pulses (which can include a spin-lock RF pulse cluster or a saturation RF pulse) can be chosen as desired, subject to Eq. (8) and, in some embodiments, the constraint that $R_{1\rho}(\omega_1, \Delta\omega)TSL<<1$. It should be understood that the RF amplitudes and off-resonance frequencies for the two acquisitions are different from each other.

In some embodiments, crusher gradients can be applied after each spin-lock pulse and prior to each signal acquisition sequence. Fat suppression and/or other preparatory pulse sequences can be applied before or after each spin-lock pulse and prior to each signal acquisition sequence. Using process 200 or similar processes, $R_{mts1}$ can be determined directly from measured magnetizations (or images), without separately measuring $R_{1\rho}^{(1)}$ and $R_{1\rho}^{(2)}$.

In some embodiments, the phase difference between the first and second images can be used to characterize motion between images. Since the phase at the same regions of the first and second images are comparable if there is no flow and/or motion occurring at that region when acquiring the two images, phase differences of the first and second images in a given region reflect flow and motion effects. This information can be used to guide the choice of image pixels and region of interest for data analysis. For example, pixels in regions with significant phase differences between the first and second images (e.g., phase differences above a preselected threshold) can be discarded in subsequent analysis.

Process 200, process 300 or other similar processes can provide a quantitative measurement of MPF that is specific to the MT effect. Other parameters of magnetization transfer, including MPF, can be computed, e.g., using equations published in U.S. Patent Application Pub. No. 2021/0141041 A1. For example, as described therein, the pool size ratio $f_b$ of the bound pool of protons can be computed from $R_{mts1}$ according to the Bloch-McConnell equations or the equation $$R_{mts1} = k_{ba}^2 f_b (1+f_b) \left( \frac{1}{(1+f_b)k_{ba} + R_{rfc}^{(1)}} - \frac{1}{(1+f_b)k_{ba} + R_{rfc}^{(2)}} \right), \quad (17)$$

where $k_{ba}$ is a magnetization exchange rate between a free-water pool and the bound pool, $R_{rfc}^{(1)}$ is a parameter representing a saturation rate of the bound pool at the first off-resonance frequency $\Delta\omega^{(1)}$ and the first RF amplitude $\omega_1^{(1)}$, and $R_{rfc}^{(2)}$ is a parameter representing a saturation rate of the bound pool at the second off-resonance frequency $\Delta\omega^{(2)}$ and the second RF amplitude $\omega_1^{(2)}$. MPF can be computed from the pool size ratio $f_b$ according to Eq. (6) above. The saturation rate parameter $R_{rfc}$ can be a function of RF amplitude ($\omega_1$), off-resonance frequency ($\Delta\omega$), and a transverse relaxation time of the bound pool ($T_{2b}$). In some embodiments, the magnetization exchange rate $k_{ba}$ and the transverse relaxation time of the bound pool $T_{2b}$ can be treated as constants that do not depend on the off-resonance frequency $\Delta\omega$ or the RF amplitude $\omega_1$.

It should be noted that $R_{mts1}$ is sensitive to MT-related parameters, including MPF, $k_{ba}$, and $T_{2b}$, while being insensitive to other confounding factors such as T1 or T2 of the free water pool. Consequently, spin-lock techniques can be used to measure MPF, $k_{ba}$, and $T_{2b}$. For example, $\Delta\omega$, $\omega_1$, and TSL can be varied to obtain multiple measurements of $R_{mts1}$, e.g., by repeating process 200 or process 300 with different values of $\Delta\omega$, $\omega_1$, and/or TSL. From these multiple measurements of $R_{mts1}$, MT-related parameters such as MPF, $k_{ba}$, and/or $T_{2b}$ can be estimated using Eq. (17) or machine learning (e.g., deep learning) methods based on the Bloch-McConnell equations.

According to some embodiments, $R_{1\rho}(\omega_1, \Delta\omega)$ can also be quantified directly using any of Eqs. (9), (10), (11), or (15) for a given frequency of spin-lock (FSL, or $\omega_1$) and frequency offset (FO, or $\Delta\omega$). After measurements of $R_{1\rho}(\omega_1, \Delta\omega)$ under different conditions of spin-lock ($\omega_1^{(1)}$, $\Delta\omega^{(1)}$) and ($\omega_1^{(2)}$, $\Delta\omega^{(2)}$) are obtained, the parameters in the quantitative magnetization transfer model of Eqs. (1) through (5), including $R_{1a}$, $R_{2a}$, $f_b$, $k_{ba}$, and $T_{2b}$, can be fitted. The following approaches can be used to simplify such a fitting process. First, $R_{1a}$ and $R_{2a}$ can be approximated as tissue R1 and R2, which can be determined using established methods. Tissue R1 can also be quantified using imaging data acquired with various $T_{rec}$ in Eq. (14). Second, FSL and FO used in spin-lock can be chosen so that $R_{1\rho}(\omega_1, \Delta\omega)$ is insensitive to $T_{2b}$, and thus $T_{2b}$ can be considered as a known constant during fitting.

Examples: Simulation Studies

Numerical simulations have been performed applying process 200 to simulated tissues of cartilage, brain, and liver. The simulation parameters used are shown in Table 2. The spin-lock parameters were chosen as: $\Delta\omega^{(1)}=800$ Hz, $\Delta\omega^{(2)}=4000$ Hz, $\omega_1^{(1)}=100$ Hz, $\omega_1^{(1)}=500$ Hz. Following off-resonance spin-lock, a crusher gradient was applied to dephase magnetization in the transverse plane.

TABLE 2

| Tissue Type | $T_{1a}$ (ms) | $T_{2a}$ (ms) | $T_{1b}$ (ms) | $T_{2b}$ (us) | $k_{ba}$ (S$^{-1}$) | $f_b$ (%) |
|---|---|---|---|---|---|---|
| Cartilage | 1168 | 27 | 1168 | 8.3 | 57 | 17.1 |
| White Matter | 1084 | 70 | 1084 | 10.0 | 23 | 14 |
| Liver | 812 | 42 | 812 | 7.7 | 51 | 6.9 |

Figure 4:
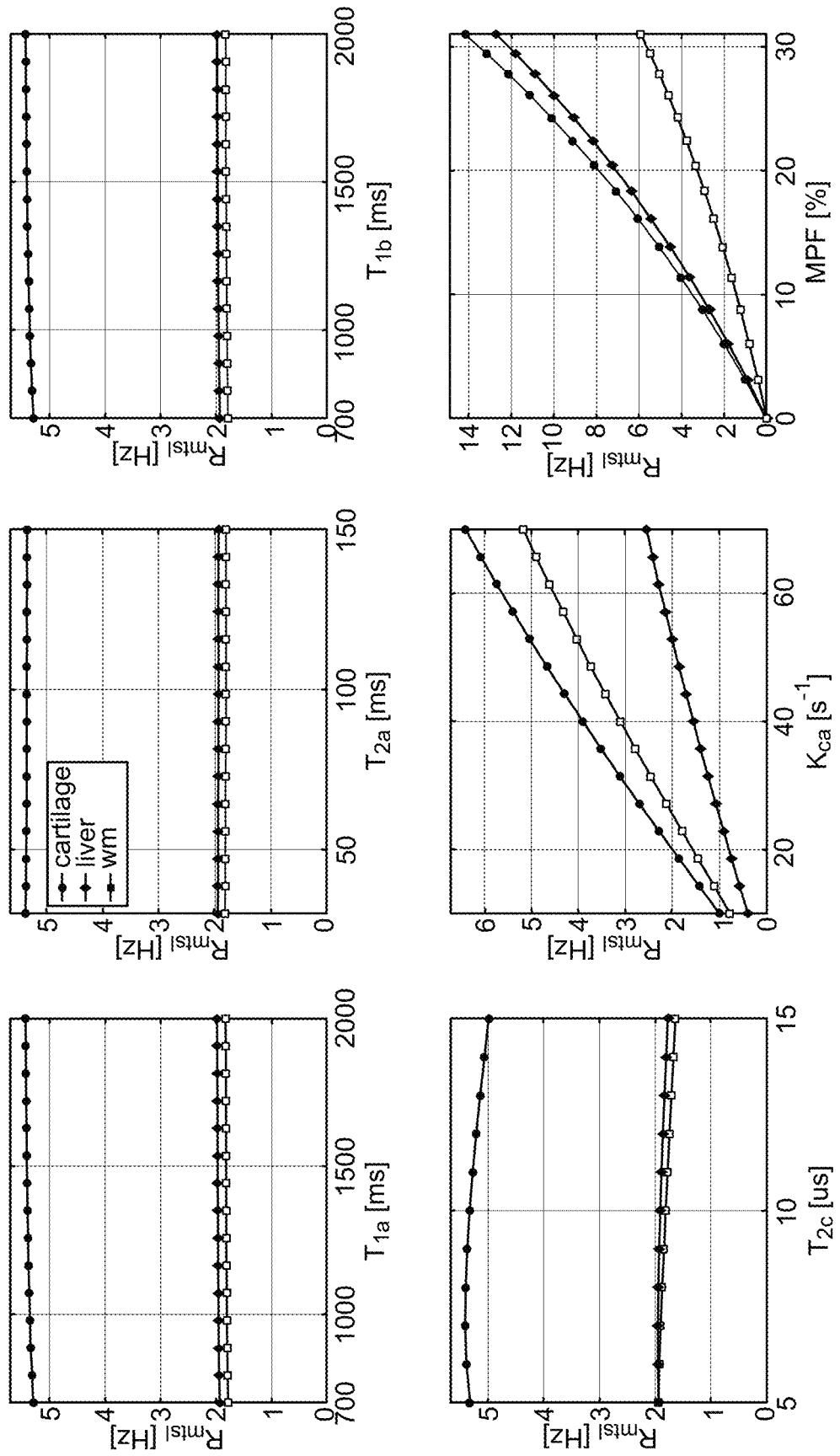
FIGS. 4-7 show graphs of results of simulation studies according to various embodiments.
Figure 5:
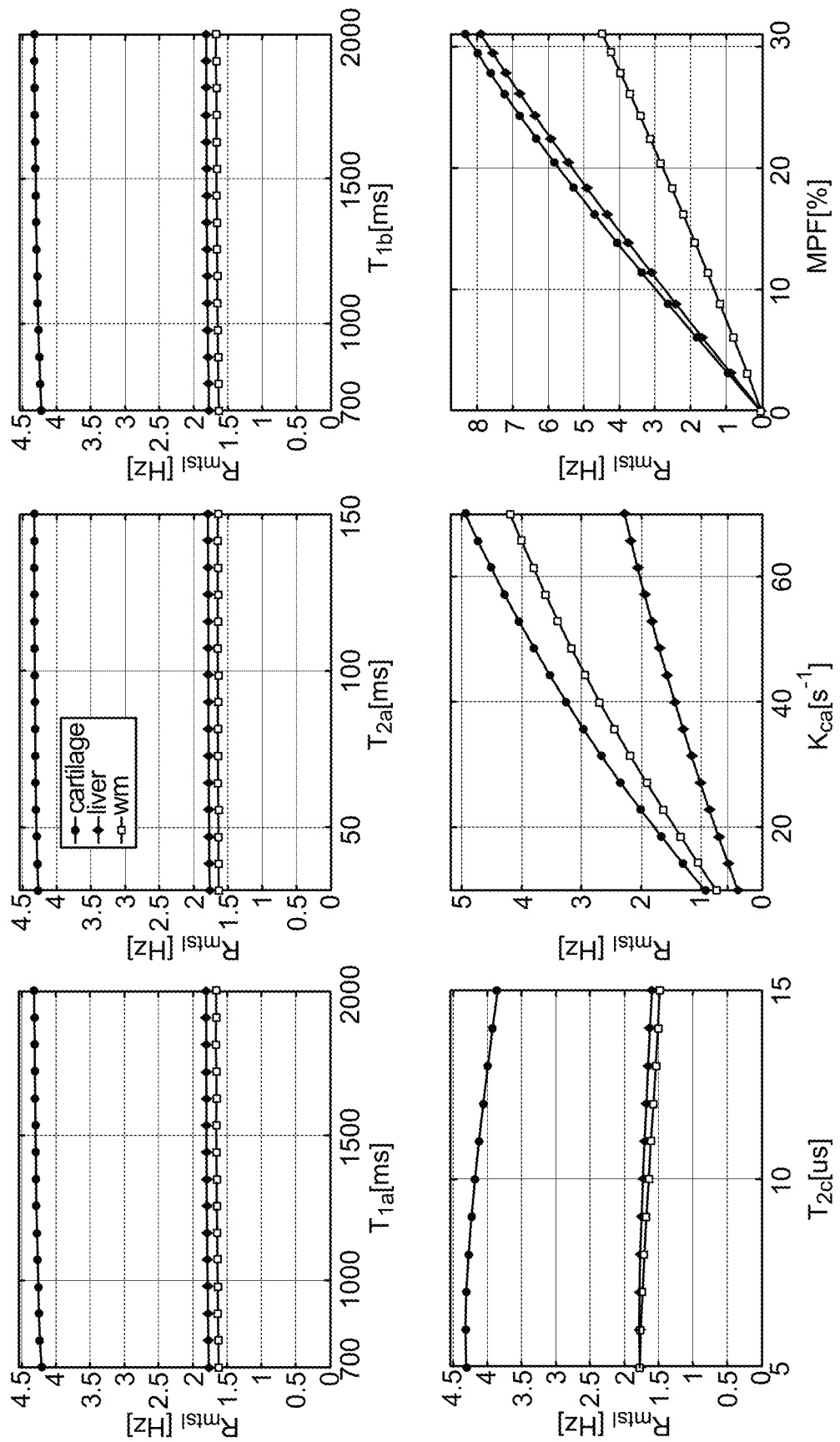

To assess sensitivity of $R_{mts1}$ to various parameters, simulations were carried out using the two-pool Bloch-McConnell simulation, with a free water pool and a MT pool described above. FIGS. 4 and 5 show the results for cartilage, white matter, and liver with varying values of the parameters $R_{1a}$, $R_{2a}$, $R_{1b}$, $R_{2b}$, $k_{ba}$, and $f_b$. In FIG. 4, $R_{mts1}$ is determined using Eq. (13), and in FIG. 5, $R_{mts1}$ is determined using Eq. (16). $R_{mts1}$ is plotted as functions of various parameters with a wide range covering in vivo conditions. As shown in FIGS. 4 and 5, $R_{mts1}$ is insensitive to the tissue parameters of the water pool but shows sensitivity to $f_b$, $k_{ca}$, and $R_{2b}$ with the spin-lock parameters used in this simulation.

Figure 6:
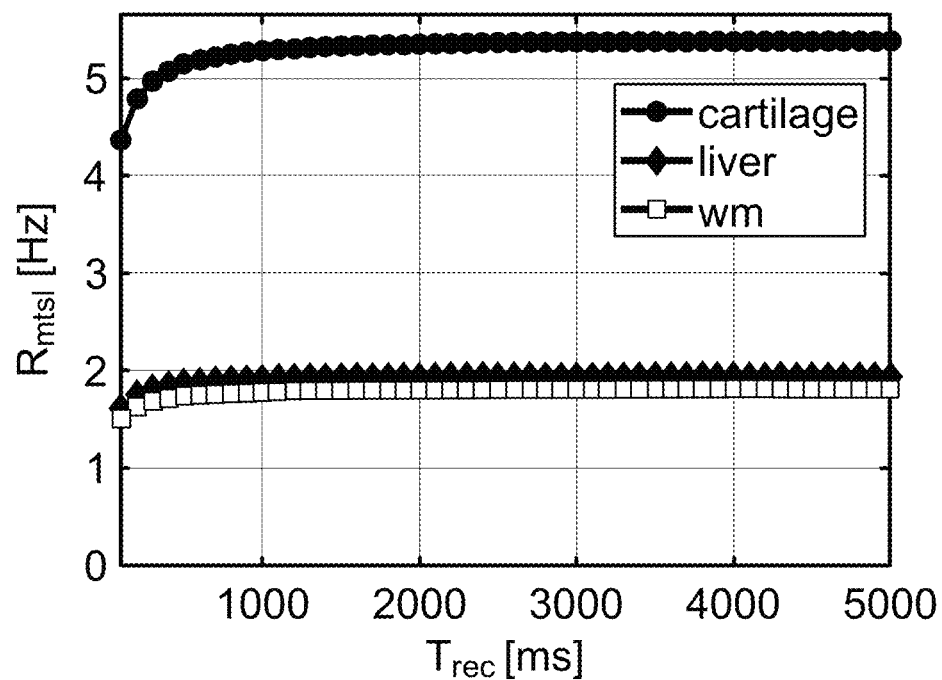
Figure 7:
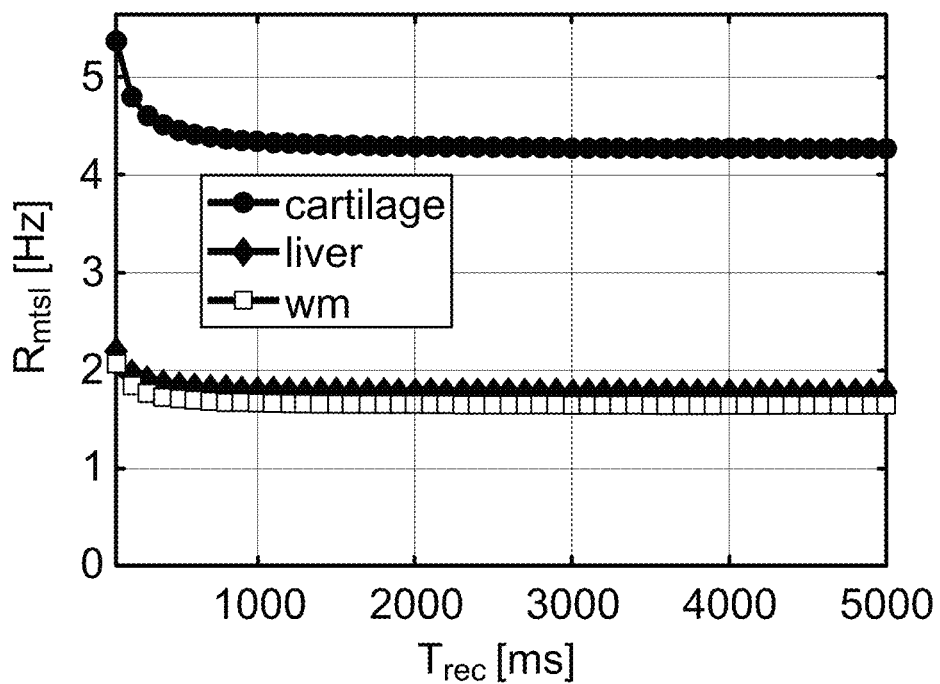

Another simulation study was performed to assess the influence of the recovery time $T_{rec}$ on MPF quantification based on Eq. (12), (13), (15) and (16). In this simulation, $T_{rec}$ was in the range of 100 ms to 5000 ms, with a step of 100 ms. Two-pool Bloch-McConnell simulations to determine $R_{mts1}$ and MPF were performed with varying $T_{rec}$. Tissue parameters used in this simulation are listed in Table 2. FIGS. 6 and 7 show the simulation results of $R_{mts1}$ for cartilage, white matter and liver. In FIG. 6, $R_{mts1}$ is determined using Eq. (13), and in FIG. 7, $R_{mts1}$ is determined using Eq. (16). As shown in FIGS. 6 and 7, $R_{mts1}$ approaches a stable value under the condition $T_{rec} > T_1$ using either Eq. (13) or Eq. (16).

Additional Embodiments

While the invention has been described with reference to specific embodiments, those skilled in the art will appreciate that numerous modifications are possible. For example, pulse sequence parameters described above can be modified, and additional pulse sequences can be incorporated as desired. Any of the above or other approaches can be used to determine $R_{mts1}$, as defined by Eq. (7), from MRI image data. MT quantification as described herein can be applied to a variety of tissue types, not limited to specific examples disclosed herein.

All processes described herein are illustrative and can be modified. Operations can be performed in a different order from that described, to the extent that logic permits; operations described above may be omitted or combined; operations described sequentially may be performed in parallel; and operations not expressly described may be added. Different processes can be used separately or together in any combination or subcombination.

In some embodiments, image analysis operations as described above can be performed in the same computer system that performs image acquisition (e.g., as described with reference to FIG. 1). In other embodiments, distributed computing systems can be used, and image data acquired using an image acquisition system (e.g., as described above with reference to FIG. 1) can be transferred to a different computer system for analysis. It should be understood that a computer systems can include hardware components of generally conventional design (e.g., processors, memory and/or other storage devices, user interface components, network interface components) and that program code or other instructions can be provided to the computer system to cause the system to perform computations and/or other processes implementing embodiments described herein or aspects thereof.

Techniques described herein can be implemented by suitable programming of general-purpose computers. A general-purpose computer can include a programmable processor (e.g., one or more microprocessors including a central processing unit (CPU) and one or more co processors such as graphics processing units (GPUs), or other co-processors optimized to implement nodes of a deep neural network) and memory to store instructions and data used by the programmable processor. A general-purpose computer can also include user interface components such as a display, speakers, keyboard or keypad, mouse, touch pad, track pad, joystick, touch screen, microphone, etc. A general-purpose computer can also include data communication interfaces to transmit data to other computer systems and/or receive data from other computer systems; examples include USB ports; Ethernet ports; other communication ports to which electrical and/or optical signal wires can be connected; and/or antennas and supporting circuitry to implement wireless communication protocols such as Wi-Fi, Bluetooth, NFC (near-field communication), or the like. In some embodiments, a computer system includes a single computer apparatus, where various subsystems can be components of the computer apparatus. The computer apparatus can have a variety of form factors including, e.g., a laptop or tablet computer, a desktop computer, etc. A computer system may include a monitor, printer or other suitable display for providing any of the results mentioned herein to a user. In other embodiments, a computer system can include multiple computer apparatuses, each being a subsystem, with internal components. A computer system can include a plurality of components or subsystems, e.g., connected together by external interface or by an internal interface. In some embodiments, computer systems, subsystems, or apparatuses can communicate over a network. For instance, a computer system can include a server with massive processing power to implement deep neural networks and a client that communicates with the server, providing instructions for specific network structures and operations.

It should be understood that any of the embodiments of the present invention can be implemented in the form of control logic using hardware (e.g., an application specific integrated circuit or field programmable gate array) and/or using computer software with a programmable processor in a modular or integrated manner. As used herein a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using a programming platform such as MATLAB, or any suitable computer language such as, for example, Java, C, C++, C #, Objective-C, Rust, Golang, Swift, or scripting language such as Perl, Python, or PyTorch, using, for example, conventional or object-oriented techniques. The software code may be stored as a series of instructions or commands on a computer readable storage medium; suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable storage medium may be any combination of such storage devices or other storage devices capable of retaining stored data. Computer readable storage media encoded with the program code may be packaged with a compatible device or provided separately from other devices. Any such computer readable storage medium may reside on or within a single computer product (e.g. a hard drive, a CD, or an entire computer system), and may be present on or within different computer products within a system or network.

Such programs may also be encoded and transmitted using carrier signals adapted for transmission via wired, optical, and/or wireless networks conforming to a variety of protocols, including the Internet. As such, a computer readable transmission medium (which is distinct from a computer readable storage medium) may be created using a data signal encoded with such programs.

Any of the methods described herein may be totally or partially performed with a computer system including one or more processors, which can be configured to perform the steps. Thus, embodiments can involve computer systems configured to perform the steps of any of the methods described herein, potentially with different components performing a respective step or a respective group of steps. Although presented as numbered steps, steps of methods herein can be performed at a same time or in a different order. Additionally, portions of these steps may be used with portions of other steps from other methods. Also, all or portions of a step may be optional. Additionally, and of the steps of any of the methods can be performed with modules, circuits, or other means for performing these steps.

The specific details of particular embodiments may be combined in any suitable manner without departing from the spirit and scope of embodiments of the invention. However, other embodiments of the invention may be involve specific embodiments relating to each individual aspect, or specific combinations of these individual aspects.

The above description is illustrative and is not restrictive. Many variations of the invention will become apparent to those skilled in the art upon review of the disclosure. The scope of patent protection should, therefore, be determined not with reference to the above description, but instead should be determined with reference to the following claims along with their full scope or equivalents.

What is claimed is:

1. A method for quantifying magnetization transfer using a magnetic resonance imaging (MRI) apparatus, the method comprising:
    performing a first image acquisition process to produce a first MR image, wherein the first image acquisition process includes applying a first off-resonance spin-lock pulse having a first RF amplitude ($\omega_1^{(1)}$), a first frequency offset ($\Delta\omega^{(1)}$), and a first time of spin-lock ($TSL^{(1)}$);
    performing a second image acquisition process to produce a second MR image, wherein the second image acquisition process includes applying a second off-resonance spin-lock pulse having a second RF amplitude ($\omega_1^{(2)}$), a second frequency offset ($\Delta\omega^{(2)}$), and a second time of spin-lock ($TSL^{(2)}$), wherein the first time of spin-lock $TSL^{(1)}$ and the second time of spin-lock $TSL^{(2)}$ are equal to the same time of spin-lock (TSL),
    wherein the first RF amplitude $\omega_1^{(1)}$, the first frequency offset $\Delta\omega^{(1)}$, the second, RF amplitude ($\omega_1^{(2)}$), and the second frequency offset ($\Delta\omega^{(2)}$) are chosen such that $\Delta\omega^{(1)}/\omega_1^{(1)}=\Delta\omega^{(2)}/\omega_1^{(2)}$ and wherein one or both of the following conditions is satisfied:
        (a) $R_{1\rho}(\omega_1, \Delta\omega)TSL \ll 1$ for each of the first spin-lock pulse and the second spin-lock pulse, wherein $R_{1\rho}(\omega_1, \Delta\omega)$ is a relaxation rate in the rotating frame for a given RF amplitude $\omega_1$ and frequency offset $\Delta\omega$; or
        (b) each of the first and second image acquisition processes includes a magnetization reset RF pulse prior to the off-resonance spin-lock pulse and a recovery time ($T_{rec}$) between the magnetization reset RF pulse and the beginning of the off-resonance spin-lock pulse is greater than a longitudinal relaxation time ($T_1$) of water protons; and
    computing, based on the first and second MR images, one or more parameters of magnetization transfer, wherein the one or more parameters of magnetization transfer include a parameter $R_{mts1}$ defined as $R_{mts1}=R_{1\rho}^{(2)}-R_{1\rho}^{(1)}$, wherein:
        $R_{1\rho}^{(1)}$ is a first relaxation rate in the rotating frame responsive to a spin-lock pulse having the first RF amplitude $\omega_1^{(1)}$ and the first frequency offset $\Delta\omega^{(1)}$; and
        $R_{1\rho}^{(2)}$ is a second relaxation rate in the rotating frame responsive to a spin-lock pulse having the second RF amplitude $\omega_1^{(2)}$ and the second frequency offset $\Delta\omega^{(2)}$,
    wherein computing the parameter $R_{mts1}$ includes computing:

$$R_{mts1} = -\log\frac{M^{(2)}}{M^{(1)}}/TSL,$$

wherein $M^{(1)}$ corresponds to the first image and $M^{(2)}$ corresponds to the second image.

2. The method of claim 1 further comprising:
    computing one or more additional parameters of magnetization transfer based on the parameter $R_{mts1}$, wherein the one or more additional parameters of magnetization transfer include a macromolecular proton fraction (MPF) indicating a fraction of protons that are bound to semi-solid macromolecules.

3. The method of claim 1 wherein computing the parameter $R_{mts1}$ includes using machine-learning based methods based on a magnetization model of each image acquisition.

4. The method of claim 1 wherein each instance of applying an off-resonance spin-lock pulse includes applying an off-resonance spin-lock RF pulse cluster that includes a hard RF pulse or an adiabatic RF pulse.

5. The method of claim 1 wherein each instance of applying an off-resonance spin-lock pulse includes applying a saturation RF pulse.

6. The method of claim 1 wherein performing each of the first and second image acquisition processes includes applying at least one preparatory pulse sequence before or after applying the spin-lock pulse and prior to acquiring data.

7. The method of claim 1 further comprising, prior to computing the one or more parameters of magnetization transfer:
    determining a phase difference between corresponding pixels of the first MR image and the second MR image; and
    discarding pixels of the first MR image and the second MR image for which the phase difference exceeds a threshold.

8. The method of claim 1 further comprising:
performing multiple instances of the first and second image acquisition processes, wherein each instance uses a different selection of RF amplitudes and frequency offsets;
separately computing a measurement of the parameter $R_{mts1}$ from each instance of the first and second image acquisition processes; and
using the separately computed measurements of the parameter $R_{mts1}$ to compute one or more of a macromolecular proton fraction (MPF), a magnetization exchange rate between a free-water pool and the bound pool ($k_{ba}$), or a transverse relaxation time of the bound pool ($T_{2b}$).

9. The method of claim 1 wherein the first MR image and the second MR image are images of a region of interest that comprises a tissue of a patient.

10. A method for quantifying magnetization transfer using a magnetic resonance imaging (MRI) apparatus, the method comprising:
performing a first image acquisition process to produce a first MR image, wherein the first image acquisition process includes applying a first off-resonance spin-lock pulse having a first RF amplitude ($\omega_1^{(1)}$), a first frequency offset ($\Delta\omega^{(1)}$), and a first time of spin-lock ($TSL^{(1)}$), wherein the first image acquisition process is used to determine a first measured magnetization $M^{(1)}$ that depends on a first relaxation rate in the rotating frame $R_{1\rho}^{(1)}$;
performing a second image acquisition process to produce a second MR image, wherein the second image acquisition process includes applying a second off-resonance spin-lock pulse having a second RF amplitude ($\omega_1^{(2)}$), a second frequency offset ($\Delta\omega^{(2)}$), and a second time of spin-lock ($TSL^{(2)}$), wherein the second image acquisition process is used to determine a second measured magnetization $M^{(2)}$ that depends on a second relaxation rate in the rotating frame $R_{1\rho}^{(2)}$ and wherein one or both of the following conditions is satisfied:
(a) $R_{1\rho}(\omega_1, \Delta\omega)TSL \ll 1$ for each of the first spin-lock pulse and the second spin-lock pulse, wherein $R_{1\rho}(\omega_1, \Delta\omega)$ is a relaxation rate in the rotating frame for a given RF amplitude $\omega_1$ and frequency offset $\Delta\omega$; or
(b) each of the first and second image acquisition processes includes a magnetization reset RF pulse prior to the off-resonance spin-lock pulse and a recovery time ($T_{rec}$) between the magnetization reset RF pulse and the beginning of the off-resonance spin-lock pulse is greater than a longitudinal relaxation time ($T_1$) of water protons;
performing a third image acquisition process to produce a third MR image, wherein the third image acquisition process includes applying a third off-resonance spin-lock pulse having a third RF amplitude ($\omega_1^{(3)}$), a third frequency offset ($\Delta\omega^{(3)}$), and a third time of spin-lock ($TSL^{(3)}$) that is equal to zero, wherein the third image acquisition process is used to determine a third measured magnetization $M_{ini}$ that represents the initial magnetization just before spin-lock; and
computing, based on the first, second, and third MR images, one or more parameters of magnetization transfer, wherein the one or more parameters of magnetization transfer include a parameter $R_{mts1}$ defined as $R_{mts1} = R_{1\rho}^{(2)} - R_{1\rho}^{(1)}$, wherein computing the parameter $R_{mts1}$ includes computing:

$$R_{mts1} = \frac{1}{TSL^{(2)}} - \frac{1}{TSL^{(1)}} + \frac{M^{(1)}TSL^{(2)} - M^{(2)}TSL^{(1)}}{M_{ini}TSL^{(1)}TSL^{(2)}}.$$

11. The method of claim 10 further comprising:
computing one or more additional parameters of magnetization transfer based on the parameter $R_{mts1}$, wherein the one or more additional parameters of magnetization transfer include one or more of:
a macromolecular proton fraction (MPF) indicating a fraction of protons that are bound to semi-solid macromolecules;
a longitudinal relaxation rate of a free-water pool ($R_{1a}$);
a transverse relaxation rate of the free-water pool ($R_{2a}$);
a pool size ration of a bound pool ($f_b$);
an exchange rate between the bound pool and the free pool ($k_{ba}$); or
a transverse relaxation rate of the bound pool ($T_{2b}$).

12. The method of claim 10 wherein computing the parameter $R_{mts1}$ includes using machine-learning based methods based on a magnetization model of each image acquisition.

13. The method of claim 10 wherein each instance of applying an off-resonance spin-lock pulse includes applying an off-resonance spin-lock RF pulse cluster that includes a hard RF pulse or an adiabatic RF pulse.

14. The method of claim 10 wherein each instance of applying an off-resonance spin-lock pulse includes applying a saturation RF pulse.

15. A magnetic resonance imaging (MRI) system comprising:
an MRI apparatus having a magnet, a gradient coil, and one or more radiofrequency (RF) coils; and
a computer communicably coupled to the MRI apparatus, the computer having a processor, a memory, and a user interface, the processor being configured to:
perform a first image acquisition process to produce a first MR image, wherein the first image acquisition process includes applying a first off-resonance spin-lock pulse having a first RF amplitude ($\omega_1^{(1)}$), a first frequency offset ($\Delta\omega^{(1)}$), and a first time of spin-lock ($TSL^{(1)}$);
perform a second image acquisition process to produce a second MR image, wherein the second image acquisition process includes applying a second off-resonance spin-lock pulse having a second RF amplitude ($\omega_1^{(2)}$), a second frequency offset ($\Delta\omega^{(2)}$), and a second time of spin-lock ($TSL^{(2)}$), wherein the first time of spin-lock $TSL^{(1)}$ and the second time of spin-lock $TSL^{(2)}$ are equal to the same time of spin-lock (TSL),
wherein the first RF amplitude $\omega_1^{(1)}$, the first frequency offset $\Delta\omega^{(1)}$, the second RF amplitude ($\omega_1^{(2)}$), and the second frequency offset ($\Delta\omega^{(2)}$) are chosen such that $\Delta\omega^{(1)}/\omega_1^{(1)} = \Delta\omega^{(2)}/\omega_1^{(2)}$ and wherein one or both of the following conditions is satisfied:
(a) $R_{1\rho}(\omega_1, \Delta\omega)TSL \ll 1$ for each of the first spin-lock pulse and the second spin-lock pulse, wherein $R_{1\rho}(\omega_1, \Delta\omega)$ is a relaxation rate in the rotating frame for a given RF amplitude $\omega_1$ and frequency offset $\Delta w$; or
(b) each of the first and second image acquisition processes includes a magnetization reset RF pulse prior to the off-resonance spin-lock pulse and a recovery time ($T_{rec}$) between the magnetization reset RF pulse and the beginning of the off-resonance spin-lock pulse is greater than a longitudinal relaxation time ($T_1$) of water protons; and compute, based on the first and second MR images, one or more parameters of magnetization transfer, wherein the one or more parameters of magnetization transfer include a parameter $R_{mts1}$ defined as $R_{mts1}=R_{1\rho}^{(2)}-R_{1\rho}^{(1)}$, wherein:

$R_{1\rho}^{(1)}$ is a first relaxation rate in the rotating frame responsive to a spin-lock pulse having the first RF amplitude $\omega_1^{(1)}$ and the first frequency offset $\Delta\omega^{(1)}$; and $R_{1\rho}^{(2)}$ is a second relaxation rate in the rotating frame responsive to a spin-lock pulse having the second RF amplitude $\omega_1^{(2)}$ and the second frequency offset $\Delta\omega^{(2)}$, wherein computing the parameter $R_{mts1}$ includes computing:

$$R_{mts1} = -\log\frac{M^{(2)}}{M^{(1)}}/TSL,$$

wherein $M^{(1)}$ corresponds to the first image and $M^{(2)}$ corresponds to the second image.

16. The system of claim 15 wherein the processor is further configured to compute one or more additional parameters of magnetization transfer based on the parameter $R_{mts1}$, wherein the one or more additional parameters of magnetization transfer include one or more of:

a macromolecular proton fraction (MPF) indicating a fraction of protons that are bound to semi-solid macromolecules;

a longitudinal relaxation rate of a free-water pool ($R_{1a}$);

a transverse relaxation rate of the free-water pool ($R_{2a}$);

a pool size ration of a bound pool ($f_b$);

an exchange rate between the bound pool and the free pool ($k_{ba}$); or a transverse relaxation rate of the bound pool ($T_{2b}$).

17. The system of claim 15 wherein the processor is further configured such that computing the parameter $R_{mts1}$ includes using machine-learning based methods based on a magnetization model of each image acquisition.

18. The system of claim 15 wherein each instance of applying an off-resonance spin-lock pulse includes applying an off-resonance spin-lock RF pulse cluster that includes a hard RF pulse or an adiabatic RF pulse.

19. The system of claim 15 wherein each instance of applying an off-resonance spin-lock pulse includes applying a saturation RF pulse.

20. The system of claim 15 wherein the processor is further configured such that performing each of the first and second image acquisition processes includes applying at least one preparatory pulse sequence before or after applying the spin-lock pulse and prior to acquiring data.

* * * * *